United States Patent [19]

Carpenter et al.

[11] Patent Number: 5,171,660
[45] Date of Patent: Dec. 15, 1992

[54] PROCESS OF REVITALIZING CELLS AND TISSUE PRIOR TO CRYOPRESERVATION

[75] Inventors: John F. Carpenter; Kelvin G. M. Brockbank, both of Marietta, Ga.

[73] Assignee: Cryolife, Inc., Marietta, Ga.

[21] Appl. No.: 344,013

[22] Filed: Apr. 26, 1989

[51] Int. Cl.$^5$ ............................................... A01N 1/02
[52] U.S. Cl. ....................................... 435/1; 435/240.1; 435/240.2
[58] Field of Search ....................... 435/1, 240.1, 240.2

[56] References Cited

U.S. PATENT DOCUMENTS 3,545,221 12/1970 Swenson et al. ..................... 435/1
3,810,367 5/1974 Peterson ............................. 435/1

FOREIGN PATENT DOCUMENTS 88109528.5 12/1988 European Pat. Off. .
8802832 8/1988 PCT Int'l Appl. .

OTHER PUBLICATIONS

Smorag et al.—Frozen Storage of Laboratory Animals, (1981), pub Verlag, N.Y., N.Y., pp. 45-53.
Taylor, M. J., et al., "Interaction of Cooling Rate, Warming Rate, and Extent of Isolated Rat Islets of Langerhans During Cryopreservation", *Diabetes*, vol. 36, pp. 59-65 (1987).
Lafferty, K. J., et al., "Prevention of Rejection by Treatment of the Graft: An Overview", *Transplantation: Aproaches to Graft Rejection*, pp. 87 to 117 (1986).
Nanchahal, J., et al., "Cultured Composite Skin Grafts: Biological Skin Equivalents Permitting Massive Expansion", *The Lancet*, Jul. 22, 1989, pp. 191-193.
Weber, C., et al., "Murine Islet Cryopreservation and Corticosteroids: Functional Studies", *Cryobiology*, 20, 219-225 (1983).
Mezzogiorno, V., et al., "Morphological Investigations into the Structure of Frozen Thawed Rat Islets of Langerhans", *Cryobiology*, 21, 296-302 (1984).
Sandler, S., et al., *Cryobiology*, 21: 503-510 (1984).
Whittingham, D. G., et al., *Science*, 178: 411-414 (1972).
Rajotte, R. V., et al., *Cryobiology*, 20: 169-184 (1983).
Cuono, C. B., et al., *Plastic & Reconstr. Surg.*, 80: No. 4, pp. 626-635, Oct. 1987.
Bank, H. L., et al., *Diabetologia*, 16, 195-199 (1979).
Calhoun, A. D., et al., *J. Surg. Res.*, 22: 687-696 (1977).
Tomford, W. W., et al., *J. Bone & Jt. Surg.*, 66-A, No. 2, (Feb. 1984).
"Cultured Composite Skin Grafts: Biological Skin Equivalents Permitting Massive Expansion", *Lancet*, vol. 2, Jun. 22, 1989, pp. 191-193.
Biological Abstract No. 46563 Shiogama, T., et al., vol. 85 (1988).

*Primary Examiner*—Sam Rosen
*Attorney, Agent, or Firm*—Kenyon & Kenyon

[57] ABSTRACT

A method of revitalizing cells or tissues that are to be cryopresrved for storage at ultracold temperatures, e.g. −196° C. is disclosed which comprises preincubation of the cells or tissue from about 5 minutes to about 24 hours. The preincubation may be conducted at a temperature ranging from about 27° C. to 42° C., after which the tissue or cells are cryopreserved.

13 Claims, 2 Drawing Sheets

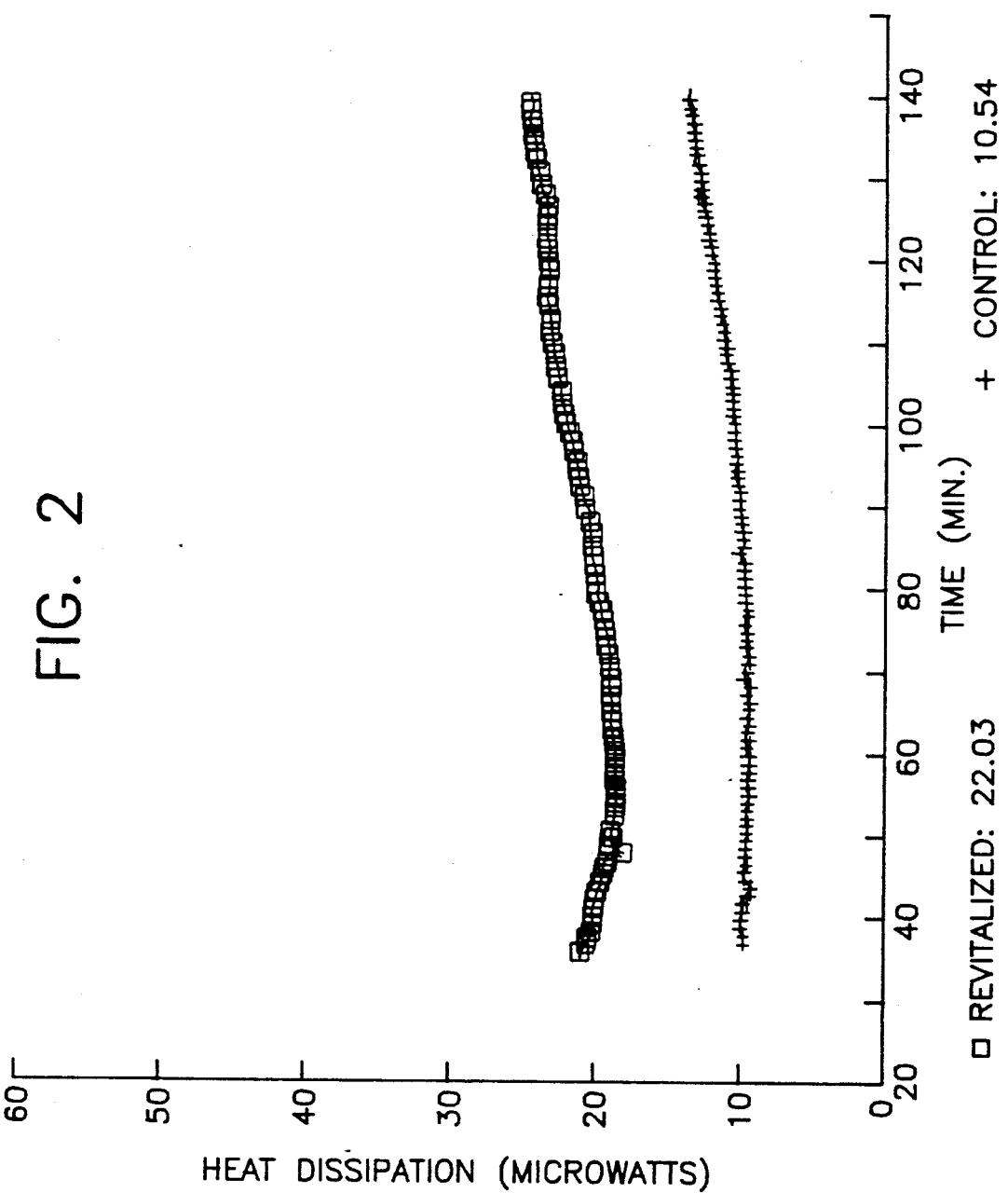

PROCESS OF REVITALIZING CELLS AND TISSUE PRIOR TO CRYOPRESERVATION

TECHNICAL FIELD

The present invention relates to a method for revitalizing cells or tissues that are to be cryopreserved for storage at ultracold temperature. Hence, the metabolic energy status and the tissue or cellular function are preserved, and maximized upon subsequent thawing and transplantation.

More particularly, the process described herein results in increased cell viability and functional capacity upon thawing. Tissue cryopreserved after this revitalization process is of much higher quality for transplantation than tissue cryopreserved without use of the revitalization process described herein.

BACKGROUND OF THE INVENTION

Current medical technology allows the use of several different types of tissue for transplantation to correct congenital, diseased-induced or degenerative failure of a recipient's tissue. Some examples include allograft human heart valves, veins, corneas, bone marrow, etc. Investigators have generally agreed that fresh tissue gives improved performance over old or dead tissue.

Human tissue remains viable in vitro for short periods of time, e.g., usually less than two to three days. Storage periods of this limited duration are usually inadequate for most tissue types due to the complexities in assuring the best match of donor to recipient (e.g. such factors as relative size of a graft, human leukocyte antigen and ABO blood group), as well as the time needed to test the tissue for pathogens. Consequently, much of the available donor tissue is unused due to the severe loss of cell viability over time. These shortcomings may be circumvented by the viable cryopreservation and ultracold storage of the tissue.

Ultracold storage of cells and tissues became possible after the discovery in 1949, by Polge, Smith and Parks, that glycerol could be used to protect cells from injury due to freezing. With the advent of low temperature biology, workers in medical and biological fields have been seeking better ways to maintain the viability of frozen donor cells or tissues.

Several methods for freezing cells and cell aggregates have been reported. For example, U.S. Pat. No. 3,303,662 discloses a process for cell preservation that utilizes a cryoprotectant in the freezing process.

The performance of a cryopreserved, transplantable tissue correlates directly with the viability of that tissue upon thawing. One parameter that provides an assessment of the cellular viability of tissue is the general metabolic energy status of the cells. In order for transplanted cells to perform their critical roles in the recipient, these cells must have sufficient metabolic capacity to carry out key energy-dependent processes. For example, one such process that is dependent on cellular metabolic energy is the biosynthesis of proteins. Furthermore, essentially any cellular, tissue or organ function is ultimately dependent on energy derived from cellular metabolism.

Cells that are metabolically and functionally suppressed after thawing may not recover sufficiently to endure the shock of transplantation into a donor, and thus may not survive.

There are several steps in the handling of human tissue for cryopreservation that can decrease the metabolic energy status and depress the energy-dependent functions of the cells. The time between death and the harvest of the tissue (warm ischemia) and the time from harvest until cryopreservation (cold ischemia) are most influential. Prolonged warm and/or cold ischemia results in cells that are severely metabolically and functionally depressed.

Cryopreservation itself appears to reduce cellular energy and metabolic capacity, and to reduce energy-dependent functions at least minimally. Hence, there is a long-standing need for a method of maintaining tissue viability post-implant and for revitalizing cells in the tissue post-harvest, such that the cells essentially completely recover from the transient metabolic lesions and loss of function induced by warm and cold ischemia. The invention therefore fulfills this long-term need for greatly improved viability, and maximizes the functional capacity of cryopreserved cells upon thawing and transplantation. In addition, revitalized cells are better able to withstand the rigors of cryopreservation.

Tissues are currently placed into solutions such as tissue culture media, Lactated Ringers, saline or Collins solution on wet ice for shipping. The concentration of compounds contained in these solutions, the time period during which the tissues are retained therein, and the temperature at which the tissues are shipped can vary widely. Due to the combined effects of these variables, and due to variations in the times of warm and cold ischemia, it is difficult to predict the degree of metabolic and functional depression for any given tissue. One important feature of the present invention is that the method improves the metabolic status, and hence the capacity to function of tissues upon transplant, even with widely varying degrees of metabolic and functional suppression.

Accordingly, it is one object of the present invention to provide a method for revitalizing cells or tissues prior to cryopreservation.

It is another object of the present invention to provide a method of enhancing transplant cell viability and functional capacity upon thawing.

It is yet another object of the present invention to provide a method that improves the ability of a cryopreserved tissue or cell to survive and function upon thawing and transplantation.

It is yet another object of the present invention to provide a method for cell revitalization that can be used concomitantly with other procedures, such as antibiotic sterilization, which may be necessary in the preparation of transplantable tissue for cryopreservation.

These and other objects, features, and advantages of the present invention will become apparent after review of the following detailed description of the disclosed embodiments and the appended claims.

SUMMARY OF THE INVENTION

The present invention encompasses a method for optimizing cell revitalization comprising placing cells into a nutrient medium and incubating said cells prior to cryopreservation, at a temperature and for a period of time effective for optimizing cell revitalization.

BRIEF DESCRIPTION OF THE FIGURES

FIG. 2 shows continuous records of heat dissipation by heart valve leaflets. Revitalized leaflet halves (□) were incubated at 37° C. for six hours and then cryopreserved and thawed as described in Example 2. The control half leaflets were (+) held at 4° C. for six hours and then cryopreserved and thawed as described in Example 2. Revitalized leaflets produce heat at a rate more than 2-times that of control, nonrevitalized leaflets.

DETAILED DESCRIPTION OF THE PREFERRED EMBODIMENT

Figure 1:
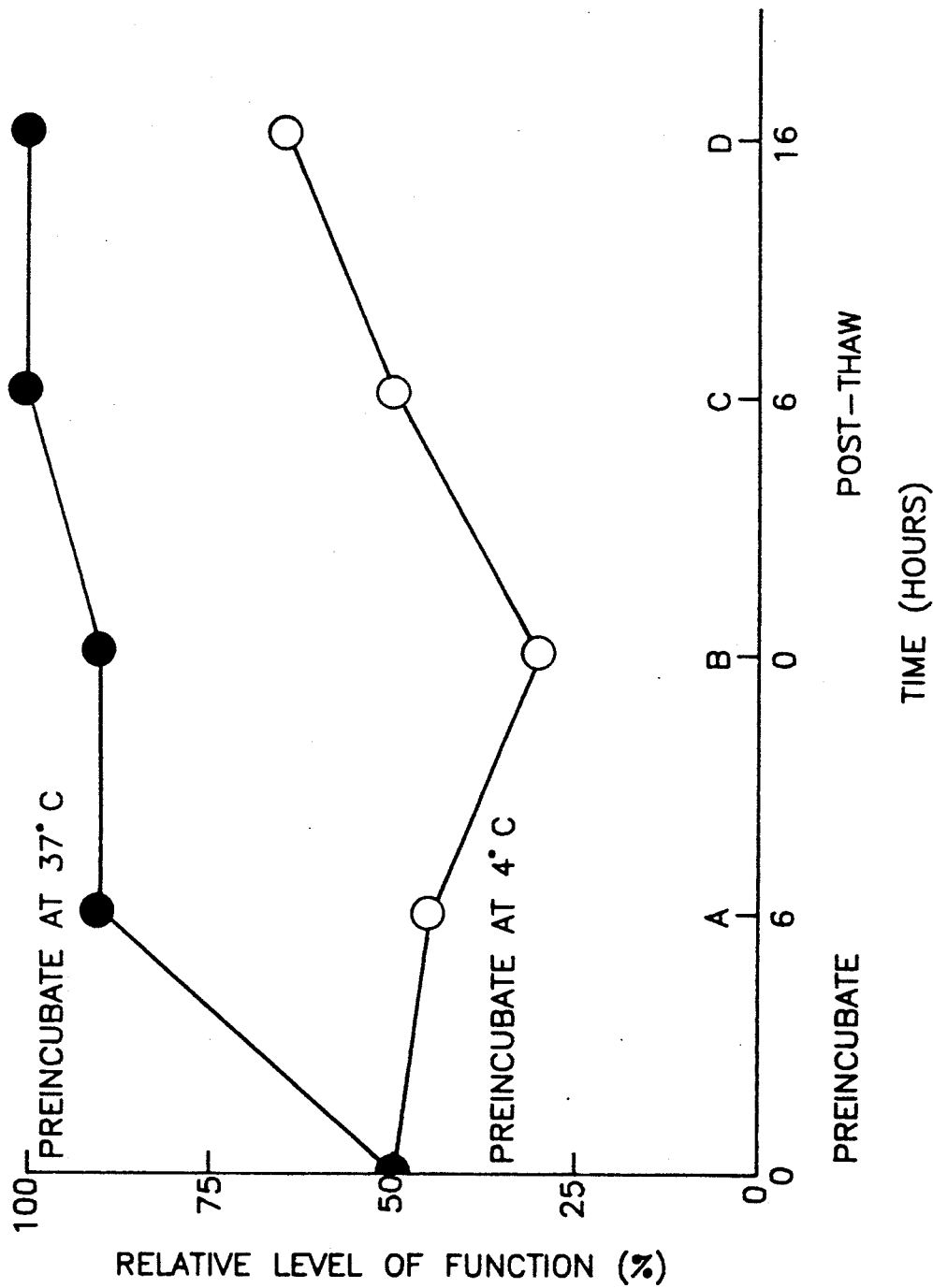
FIG. 1 discloses the cellular energy and functional status of cells following preincubation, cryopreservation, thawing and post-thaw incubation. The FIG. compares cellular energy and functional status of tissue that is held at 4° C. prior to cryopreservation to that of tissue that is revitalized (preincubated at 37° C.) in accordance with the preferred embodiment of the present invention. Time O for preincubation represents the hypothetical decrease of cellular metabolic and functional status to 50% of that seen for tissue in situ. This decrease is attributed to the combined effects of warm and cold ischemia, prior to preincubation.

The present method for revitalizing tissue or cells assures increased cellular viability and functional capacity upon thawing. The tissues, which are typically metabolically and functionally depressed by exposure to various durations of warm and cold ischemia, are treated in a manner that fosters recovery from these transient, ischemia-induced lesions. Since it is usually not practical to remove tissue immediately after donor death, nor is it usually possible to cryopreserve the tissue immediately after procurement, periods of warm and/or cold ischemia are unavoidable in the processing of human tissue for viable cryopreservation. By treating the tissue prior to cryopreservation, the method of the present invention assures that the metabolic energy status and functional capacity of the tissue are restored.

As used herein, the term "revitalization" means restoration or optimization of cellular or tissue metabolic processes and energy-dependent functions after cryopreservation, accomplished by treating the cells or tissue prior to cryopreservation. Tissue and cellular function are ultimately dependent upon cellular metabolism. Hence, cell/tissue viability and functional capacity are optimized upon transplant to maximize the transplant success rate. Revitalization measurement as used herein is not limited to specified metabolic effects or pathways, and any measure of metabolic activity or tissue or cellular function can be used. For example, protein synthesis, vascular constriction, nerve conductivity, muscle contractility, radioactive precursor uptake, radioactive or fluorescent metabolite production as well as other measures of metabolic activity or processes dependent on metabolic energy can be evaluated.

The methods described herein apply to cells and tissue as well as organs which are to be transplanted, and are not limited to specific forms of transplantable tissue. Examples include bone marrow cells, tendon, ligament, islet cells, fibroblasts, cornea, blood vessel, heart, liver, embryo, etc. The terms "cells," "tissue" and "organ" when referring to the transplantable material described herein are therefore used in the most general sense, and are used interchangeably to refer to cells, tissues, organs, etc.

Upon receipt in the laboratory, the tissue of choice is dissected away from any unwanted tissue and placed into a suitable tissue culture medium, in a container that allows for sufficient oxygenation of the medium. The tissue and medium are placed into an incubator, or a shaking water bath for an effective length of time and at an effective temperature to optimize or maximize cell or tissue viability after the sample has undergone cryopreservation and has thawed and been prepared for transplant into a patient in need for such treatment.

A number of tissue and/or cell culture media can be used successfully in practicing the present invention. Media, such as balanced tissue culture media or simple phosphate buffered saline (supplemented with a nutrient such as glucose), can be used for most tissue types. In addition, a protein suspension, such as blood serum or artificial serum may be present in the media.

Revitalization is conducted for an effective time period and at a temperature which is effective for revitalizing the tissue, thereby maximizing transplant effectiveness.

The treatment time required for revitalization may range from about 5 minutes to about 24 hours, with the preferred time being about 30 minutes to 9 hours. The most preferred time for revitalization is about 6 hours.

The temperature at which the tissue is treated ranges from about 27° C. to about 42° C., with about 35° C. to about 40° C. being preferred. The optimal temperature for revitalization is 37° C.

Following the revitalization procedure, the tissue is cryopreserved following the standard methods, in the chosen solutions, and optionally in the presence of the cryoprotectant(s) that have been shown to be optimal for each given tissue.

The frozen tissue is stored at ultracold temperatures (e.g. −196° C. in liquid nitrogen). The thawing and dilution steps typically are those which have been shown to be optimal for the given tissue. The metabolic and functional advantage (relative to non-revitalized tissue) gained by revitalizing the tissue prior to cryopreservation will be maintained after the thawing and dilution steps.

One of the advantages of the present invention is that regardless of the cryopreservation procedure followed, treating the tissue prior to freezing results in improved tissue quality (relative to non-revitalized tissue) upon thawing.

The following specific examples will illustrate the invention as it applies to the revitalization of human heart valve tissue prior to cryopreservation, and the maintenance of this metabolic and functional advantage after thawing and dilution. However, as described above, it will be appreciated that these teachings apply to all transplantable tissues; various alternatives will be apparent to those of ordinary skill in the art from the teachings herein, and the invention is not limited to the specific illustrative examples.

EXAMPLE 1

Hearts were procured in toto and shipped to the laboratory. In preparation for transport, each heart was placed into a sterile intestinal bag with about 350 ml of Lactated Ringers, saline or Collins solution. The bag was secured with a plastic band or umbilical tape and was placed into a second intestinal bag, which was likewise secured. The heart, which is thus double bagged, was placed in a plastic container and the lid secured. The container was then put into a third sterile intestinal bag and put into a styrofoam shipping container with wet ice. Upon receipt, the aortic and/or pulmonary valves were dissected and placed in the original shipping solution.

The valves were stored at 4° C. for 4 to 72 hours. Following this storage period, the valve leaflets were dissected out, and each leaflet was cut into two equal parts. The valve leaflet pieces were placed into Dulbecco's Modified Eagle's Medium ("DMEM") (low glucose, with 10% fetal calf serum) in sterile tissue culture tubes and stored on ice. One half of each leaflet was left in this solution on ice. The other half of the leaflet was transferred into a sterile tissue culture tube, which contained the same solution, but which had been warmed to 37° C. The sterile tubes containing these half leaflets were placed into a 37° C. incubator. After six hours all leaflet halves were assayed for cell viability and functionality.

The assay measured the incorporation of $^3$H 2-deoxyglucose into 2-deoxyglucose-6-phosphate by leaflet cells. This assay determines the integrity of the cell membrane, the functional capacity of the transmembrane glucose transport proteins, the integrity of the hexokinase enzymes and the general energy status of the cell. The last parameter is important because ATP is needed for the 2-deoxyglucose to be phosphorylated.

The half leaflets were placed into approximately 2 ml of sterile Hanks solution at room temperature for 3-5 minutes. They were then transferred into 0.5 ml of Hanks (at 37° C. in a heating block) containing 10 $\mu$Ci/ml $^3$H 2-deoxyglucose. After a 30 minute incubation, the half leaflets were immediately transferred to approximately 10 mls of ice cold Hanks solution. The solution was aspirated off with a pippette and another 10 mls of Hanks added. This washing procedure, which removes any extracellular 2-deoxyglucose and washes out any intracellular 2-deoxyglucose that is not phosphorylated, was repeated 4 more times. The half leaflets were then placed in 0.5 ml of 1M NaOH and incubated at 60° C. for 30 minutes. The tissue was then homogenized by sonication, and the resulting homogenate was centrifuged for 10 minutes in a table top Eppendorf centrifuge. The disintegrations per minute ("$^3$H DPM") in the resulting supernatant were determined by liquid scintillation counting. All values for $^3$H DPM were normalized for the amount of protein present in the supernatant. The results are given in Table A.

TABLE A

Comparison of 2-deoxyglucose incorporation (DPM/mg protein) by half leaflets given a six hour incubation at 37° C. to the incorporation by half leaflets held at 4° C. for six hours.

| DPM Values for Tissue Preincubated at: | | % 37° C. vs. 4° C. |
|---|---|---|
| 4° C. | 37° C. | (37° C./4° C. × 100) |
| 138,431 | 318,742 | 230 |
| 132,568 | 364,123 | 274 |
| 261,695 | 302,192 | 115 |
| 258,983 | 430,819 | 166 |
| 197,876 | 451,193 | 228 |
| 202,518 | 318,179 | 157 |
| 116,452 | 144,760 | 124 |
| 109,274 | 307,184 | 281 |
| 131,514 | 367,644 | 280 |
| | | $\bar{x} \pm SE = 206 \pm 21\%$ |

The data demonstrates that there is an approximately 2-fold improvement in cell viability and functional capacity when the tissue is revitalized by incubation at 37° C. relative to tissue incubated at 4° C. This difference is presented diagrammatically at point A. Such results show that postischemic revitalization at 37° C. leads to recovery of the cells from transient, ischemia-induced metabolic lesions and from the concomitant depression of cellular function. Thus, the data indicate that revitalization at 37° C. markedly improves the metabolic energy status and function of the cells, and hence the overall quality of the fresh human heart valve leaflets.

EXAMPLE 2

Heart valve half leaflets were prepared and incubated at 4° C. or 37° C. as described in Example 1. These half leaflets were then cryopreserved, essentially via the method described in U.S. application Ser. No. 000,095. The frozen leaflets were stored at −196° C. for at least 16 hours. The leaflets were thawed, and the cryoprotectant was diluted as described in the aforementioned patent application. Immediately after thawing and dilution, the half leaflets were assayed for 2-deoxyglucose incorporation as described in Example 1. The results are shown in Table B.

TABLE B

Comparison of 2-deoxyglucose incorporation (DPM/mg protein) by half leaflets given a six hour incubation at 37° C. vs. half leaflets given a six hour incubation at 4° C. After the incubations all leaflets were cryopreserved, thawed, diluted and immediately assayed.

| DPM Values for Tissue Preincubated at: | | % 37° C. vs. 4° C. |
|---|---|---|
| 4° C. | 37° C. | (37 C./4 C. × 100) |
| 27,281 | 70,372 | 258 |
| 34,219 | 118,682 | 347 |
| 33,944 | 86,439 | 255 |
| 132,447 | 185,887 | 140 |
| 82,604 | 320,953 | 389 |
| 162,623 | 201,013 | 124 |
| 3000 | 9493 | 316 |
| 3949 | 17,215 | 436 |
| 3990 | 14,366 | 360 |
| 13,975 | 28,888 | 207 |
| 14,960 | 38,016 | 254 |
| 16,052 | 17,130 | 107 |
| 5193 | 18,951 | 365 |
| 17,320 | 29,482 | 170 |
| 2489 | 20,533 | 825 |
| | | $\bar{x} \pm SE = 304 \pm 44\%$ |

The data demonstrates that the revitalization of tissue by incubation at 37° C. for six hours, prior to cryopreservation, results in approximately a 3-fold greater cellular viability and functional capacity than that noted when tissue is given a pre-cryopreservation incubation at 4° C. This difference is presented diagrammatically at point B. The revitalization at 37° C. leads to recovery of the cells from transient, ischemia-induced metabolic lesions and functional depression, and the improved metabolic state and functional capacity are maintained after cryopreservation and thawing. Thus, revitalization at 37° C. markedly improves the metabolic energy status and function, and hence the overall quality of the cryopreserved and thawed tissue.

EXAMPLE 3

Human heart valve leaflets were treated as described in Example 2, except that after thawing and dilution, all of the leaflet halves were placed in DMEM (low glucose with 10% fetal calf serum) and given a 6 hour post-thaw incubation at 37° C. After this incubation period, the half leaflets were assayed for 2-deoxyglucose incorporation as described in Example 1. The results are shown in Table C.

| DPM Values for Tissue Preincubated at: | | % 37° C. vs. 4° C. |
|---|---|---|
| 4° C. | 37° C. | (37° C./4° C. × 100) |
| 109,009 | 171,963 | 158 |

| DPM Values for Tissue Preincubated at: | | % 37° C. vs. 4° C. |
|---|---|---|
| 4° C. | 37° C. | (37° C./4° C. × 100) |
| 79,676 | 103,058 | 129 |
| 148,937 | 176,034 | 118 |
| 127,787 | 459,873 | 360 |
| 150,302 | 239,906 | 160 |
| 119,150 | 224,751 | 189 |
| | | x̄ ± SE = 186 ± 33% |

The data shows that the revitalization of tissue by incubation at 37° C. prior to cryopreservation, results in approximately a two fold greater cellular viability than that noted when tissue is given a pre-cryopreservation incubation at 4° C., even after the tissue has been given a six hour post-thaw incubation at 37° C. This difference is presented diagrammatically at point C. Such results show that postischemic revitalization at 37° C. leads to recovery of the cells from transient, ischemia-induced metabolic lesions and functional depression, and that the improved metabolic state and functional capacity are maintained after cryopreservation, thawing, and incubation. Thus, the data indicates that revitalization at 37° C. markedly improves the metabolic energy status and functional capacity, and hence the overall quality of the cryopreserved and thawed tissue. Furthermore, these results show that revitalized tissue would have a marked advantage over non-revitalized tissue during the first six hours after transplantation.

EXAMPLE 4

Human heart valve leaflets were treated as described in Example 2, except that after thawing and dilution, all of the leaflet halves were placed in DMEM (low glucose with 10% fetal calf serum) and given a 16 hour post-thaw incubation at 37° C. After this incubation period, the half leaflets were assayed for 2-deoxyglucose incorporation as described in Example 1. The results are shown below in Table D.

TABLE D

Comparison of 2-deoxyglucose incorporation (DPM/mg protein) by half leaflets given a six hour incubation at 37° C. vs. half leaflets given a six hour incubation at 4° C. After the incubations all leaflets were cryopreserved, thawed, diluted and then given a 16 hour post-thaw incubation at 37° C. After this incubation, the half leaflets were assayed for 2-deoxyglucose incorporation.

| DPM Values for Tissue Preincubated at: | | % 37° C. vs. 4° C. |
|---|---|---|
| 4° C. | 37° C. | (37° C./4° C. × 100) |
| 35,988 | 112,025 | 311 |
| 72,313 | 88,043 | 122 |
| 295,436 | 479,791 | 162 |
| | | x̄ ± SE = 198 ± 47% |

These results indicate that revitalized heart valve leaflets maintain their functional advantage over non-treated tissue even after 16 hours, post-thaw, at 37° C. This difference is presented diagrammatically at point D.

EXAMPLE 5

Heart valve leaflets were processed as described in Example 2, except that pre-cryopreservation incubation of three hours duration at 37° C. was compared to a three hour incubation at 4° C. The results are shown in Table E.

TABLE E

Comparison of 2-deoxyglucose incorporation (DPM/mg protein) by half leaflets given a three hour incubation at 37° C. vs. half leaflets given a three hour incubation at 4° C. After the incubations all leaflets were cryopreserved, thawed, diluted and immediately assayed.

| DPM Values for Tissue Preincubated at: | | % 37° C. vs. 4° C. |
|---|---|---|
| 4° C. | 37° C. | (37° C./4° C. × 100) |
| 10,488 | 26,062 | 248 |
| 19,839 | 34,172 | 172 |
| 18,873 | 33,169 | 176 |
| 44,872 | 54,130 | 121 |
| 58,496 | 56,509 | 97 |
| 57,270 | 61,499 | 107 |
| | | x̄ ± SE = 154 ± 21% |

The data show that the revitalization of tissue by incubation at 37° C. for three hours, prior to cryopreservation, results in approximately 1.5-fold greater cellular viability than that noted when tissue is given a pre-cryopreservation incubation at 4° C. Such results show that post-ischemic revitalization at 37° C., which can be accomplished in as little as three hours, leads to recovery of the cells from transient ischemia-induced metabolic lesions and functional depression, and that the improved metabolic state and functional capacity are maintained after cryopreservation and thawing. Thus, revitalization at 37° C. for three hours markedly improves the metabolic energy status and functional capacity, and hence the overall quality of the cryopreserved and thawed tissue.

EXAMPLE 6

Human heart valve leaflets were treated as described in Example 4, except that after thawing and dilution, all of the leaflet halves were placed in DMEM (low glucose with 10% fetal calf serum) and given a 6 hour post-thaw incubation at 37° C. After this incubation period, the half leaflets were assayed for 2-deoxyglucose incorporation as described in Example 1. The results are shown in Table F.

TABLE F

Comparison of 2-deoxyglucose incorporation (DPM/mg protein) by half leaflets given a three hour incubation at 37° C. vs. half leaflets given a three hour incubation at 4° C. After the incubations all leaflets were cryopreserved, thawed, diluted and then given a 6 hour post-thaw incubation at 37° C. After this incubation, the half leaflets were assayed for 2-deoxyglucose incorporation.

| DPM Values for Tissue Preincubated at: | | % 37° C. vs. 4° C. |
|---|---|---|
| 4° C. | 37° C. | (37° C./4° C. × 100) |
| 13,196 | 20,852 | 158 |
| 11,364 | 17,760 | 156 |
| 7320 | 25,237 | 345 |
| 201,917 | 297,080 | 147 |
| 186,465 | 280,580 | 150 |
| 185,035 | 226,723 | 123 |
| | | x̄ ± SE = 180 ± 31% |

The data shows that the revitalization of tissue by incubation at 37° C. for three hours prior to cryopreservation results in approximately 2-fold greater cellular viability than that noted when tissue is given a pre-cryopreservation incubation at 4° C., even after the tissue has been given a six hour post-thaw incubation at 37° C. Such results show that post-ischemic revitalization at 37° C. leads to recovery of the cells from transient, ischemia-induced metabolic lesions and functional depression, and that the improved metabolic state, and functional capacity are maintained after cryopreservation thawing, and incubation at physiological temperature. Thus, revitalization at 37° C. markedly improves the metabolic energy status and functional capacity and hence, the overall quality of the cryopreserved and thawed human heart valve leaflets. Furthermore, these results show that revitalized tissue would have a marked advantage over non-revitalized tissue within the first six hours after transplantation.

EXAMPLE 7

Heart valve leaflets are treated as described in Example 2, except that after thawing and dilution, two revitalized leaflet halves (preincubated at 37° C. for six hours prior to cryopreservation), from the same valve are rinsed briefly with Hanks and placed into an open-flow microcalorimeter and perfused with Hanks at a flow rate of 15 ml/minute. The tissue chamber is maintained at 37° C., and heat dissipation by the tissue is recorded continuously for a 2 hour period. The two control leaflet halves (preincubated at 4° C. prior to cryopreservation) are thawed, diluted and treated in an identical manner.

The rate of heat dissipation by the revitalized leaflet halves upon thawing is more than 2-times the rate seen with the control, nonrevitalized leaflet halves, as shown in FIG. 2. The mean heat dissipation for revitalized leaflet halves is 22.03 microwatts, whereas that for control nonrevitalized leaflet halves is 10.54 microwatts. Heat dissipation correlates directly with the metabolic energy flow of cells. Therefore, the metabolic energy flow, and hence the capacity of the tissue to function, is more than 2-times greater in revitalized leaflet halves than in control, nonrevitalized leaflet halves. This is in close agreement with the results seen when 2-deoxyglucose incorporation is used as a measurement of relative metabolic energy status and functional capacity (i.e., Example 2). Thus, by two independent measurements of tissue metabolic energy status and functional capacity it is determined that revitalized tissue is far superior to nonrevitalized tissue after thawing.

EXAMPLE 8

Whole hearts are procured and shipped to the laboratory as described in Example 1. The aortic and pulmonary valves are dissected out, placed in a tissue culture medium (e.g. DMEM with glucose) and incubated at 37° C. for about 3 to about 24 hours. If desired, antibiotics may be included in the incubation solution. After the incubation and concomitant revitalization, the valves are cryopreserved via the protocol described in U.S. application Ser. No. 000,095 which is incorporated herein by reference. Upon transplantation, such valves are of superior quality to those that had not been revitalized prior to cryopreservation.

In summary, the revitalization of tissue for about 5 minutes to about 24 hours prior to cryopreservation results in approximately 2 to 3 fold greater cellular viability than that noted when tissue is given a pre-cryopreservation incubation at 4° C., even when compared to tissue which has been given a six to sixteen hour post-thaw incubation at 37° C. Hence, post-ischemic revitalization leads to recovery of the cells from transient, ischemia-induced metabolic lesions and depressed functional capacity. The improved metabolic state and functional capacity are maintained after cryopreservation, thawing, and incubation. Revitalization markedly improves the metabolic energy status, cellular function and hence, the overall quality of the cryopreserved and thawed tissue. Furthermore, these results show that revitalized tissue would have a marked advantage over non-revitalized tissue upon transplant.

While the invention herein is described in detail, numerous alternative embodiments are possible and fall within the appended claims. Consequently, the scope of the invention is not to be limited thereby.

We claim:

1. In a process for freeze preservation of transplantable tissue in the presence of a cryoprotectant, the improvement comprising incubating said tissue, prior to freezing and prior to addition of said cryoprotectant, in a nutrient medium at a temperature of from about 27° C. to about 42° C. and for a period of time of from about 5 minutes to about 24 hours wherein upon thawing and use the transplantable tissue has improved viability and/or functional capacity over transplantable tissue not subjected to such an incubation.

2. The method of claim 1 wherein said transplantable tissue in incubated for about three to about nine hours.

3. The method of claim 2 wherein said transplantable tissue is incubated for about 6 hours.

4. The method of claim 1 wherein said transplantable tissue is incubated at 37° C.

5. The method of claim 1 wherein the nutrient medium is in the form a solution.

6. The method of claim 1 wherein the nutrient medium contains an antibiotic.

7. The method of claim 1 wherein the transplantable tissue is cardiovascular tissue.

8. The method of claim 1 wherein the transplantable tissue is incubated at about 35° C. to about 40° C.

9. The method of claim 6 wherein the transplantable tissue is incubated at about 35° C. to about 40° C.

10. The method of claim 5 wherein the transplantable tissue is incubated at about 37° C.

11. The method of claim 6 wherein the transplantable tissue is cardiovascular tissue.

12. In a method of transplanting a tissue which has been frozen in the presence of a cryoprotectant and thawed prior to transplant, and which has been subjected to warm and/or cold periods of ischemia prior to freezing, the improvement which comprises incubating said tissue, prior to freezing and prior to addition of said cryoprotectant, in a nutrient medium at a temperature of from about 27° C. to about 42° C. and for a period of time of from about 5 minutes to about 24 hours wherein upon thawing and use the transplantable tissue has improved viability and/or functional capacity over transplantable tissue not subjected to such an incubation.

13. The method of claim 12 wherein the warm and cold periods of ischemia occur prior to incubation.

* * * * *

UNITED STATES PATENT AND TRADEMARK OFFICE
CERTIFICATE OF CORRECTION

PATENT NO. : 5,171,660
DATED : December 15, 1992
INVENTOR(S) : John F. Carpenter and Kelvin G. M. Brockbank It is certified that error appears in the above-identified patent and that said Letters Patent is hereby corrected as shown below:

Column 6, line 63, after "Table C." enter the following paragraph, -- TABLE C  Comparison of 2-deoxyglucose incorporation (DPM / mg protein) by half leaflets given a six hour incubation at 37°C vs. half leaflets given a six hour incubation at 4°C. After the incubations, all leaflets were cryopreserved, thawed, diluted and then given a 6 hour post-thaw incubation at 37°C. After this incubation, the half leaflets were assayed for 2-deoxyglucose incorporation.--.  Column 10, line 43, delete "5" and replace it with -- 6 --.

Signed and Sealed this

Twenty-third Day of November, 1993

Attest:

BRUCE LEHMAN

Attesting Officer  Commissioner of Patents and Trademarks